United States Patent [19]

Nix et al.

[11] Patent Number: 5,473,161
[45] Date of Patent: Dec. 5, 1995

[54] METHOD FOR TESTING CARBONATION LOSS FROM BEVERAGE BOTTLES USING IR SPECTROSCOPY

[75] Inventors: John A. Nix, Atlanta; Stephen W. Zagarola, Woodstock, both of Ga.; Louis Jolie, Dongen, Netherlands

[73] Assignee: The Coca-Cola Company, Atlanta, Ga.

[21] Appl. No.: 262,846

[22] Filed: Jun. 21, 1994

[51] Int. Cl.⁶ ................................................ G01N 21/00
[52] U.S. Cl. ............................................................. 250/343
[58] Field of Search ............................................... 250/343

[56] References Cited

U.S. PATENT DOCUMENTS

| | | | |
|---|---|---|---|
| 3,765,533 | 10/1973 | Stephens et al. | 209/3.1 |
| 4,327,574 | 5/1982 | Alberghini et al. | 73/19.1 |
| 4,368,980 | 1/1983 | Aldred et al. | 356/240 |
| 4,517,135 | 5/1985 | Szerenyi et al. | 261/104 |
| 4,794,255 | 12/1988 | Miyatake et al. | 250/343 |
| 4,889,992 | 12/1989 | Hoberman | 250/343 |
| 5,144,831 | 9/1992 | Hale et al. | 73/19.05 |
| 5,155,019 | 10/1992 | Sussman et al. | 435/34 |

*Primary Examiner*—Constantine Hannaher

[57] ABSTRACT

A method for measuring carbonation loss in beverage bottles and predicting shelf-life thereof utilizes infrared (IR) absorption spectroscopy. The concentration of $CO_2$ gas in a bottle being tested is measured with an infrared beam according to Beer's Law. In one embodiment the $CO_2$ gas measured is in the headspace of a test bottle partially filled with carbonated water. The walls of the bottle are clamped in a fixture to maintain the bottle diameter substantially constant. An IR beam is transmitted through the bottle just below the fixture, and absorption values of the beam are measured. Shelf-life is calculated from the absorption values. In another embodiment the test bottle is filled with compressed $CO_2$ gas generated by dry ice placed in the bottle.

18 Claims, 4 Drawing Sheets

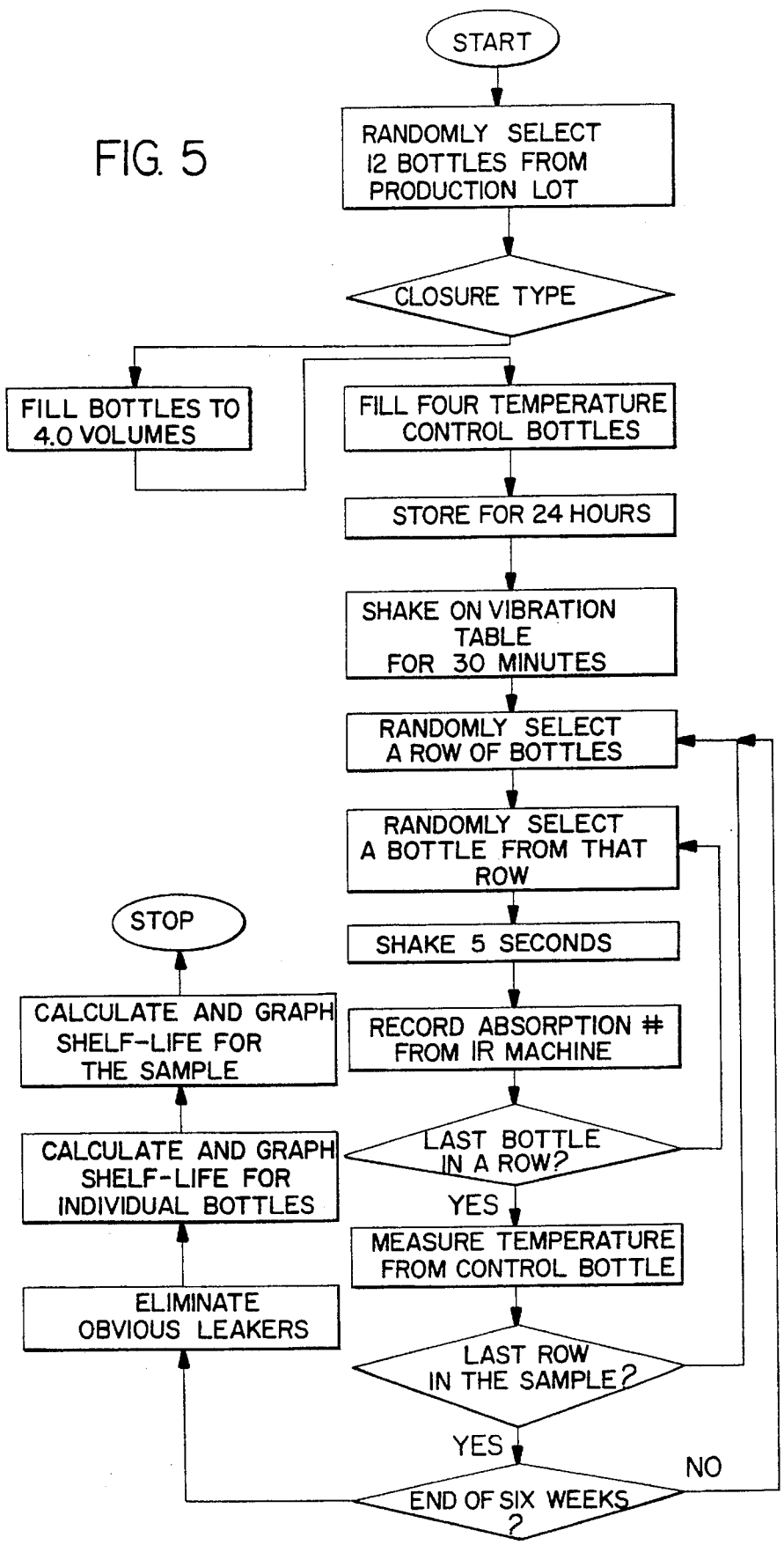

METHOD FOR TESTING CARBONATION LOSS FROM BEVERAGE BOTTLES USING IR SPECTROSCOPY

BACKGROUND OF THE INVENTION

The present invention relates to a method for testing a carbonated beverage bottle, such as a PET bottle, for carbonation loss using infrared (IR) spectroscopy. More specifically, the present invention relates to a method for predicting the shelf-life of beverage bottles with respect to carbonation retention by taking periodic readings of $CO_2$ concentration in the bottle, recording data related to infrared absorption and predicting shelf-life from the data.

Various methods are known for testing carbonation loss in beverage bottles. One well known method employs the techniques referred to as the Zahm and Nagel Test which measures pressure loss in the bottles and correlates the pressure loss to carbonation loss.

Other methods of measuring carbonation loss in beverage bottles are known which utilize infrared absorption to measure the loss of carbon dioxide from the bottles. One such method measures the rate of loss of carbon dioxide per bottle per day by measuring the amount of $CO_2$ permeating from the bottle with a sensitive infrared detector.

Another method utilizes a liquid sample cell wherein the carbonated liquid from the bottle under test is passed through the sample cell and attenuated total reflection of infrared radiation is detected. However, this test is destructive of the bottle or package. The closure must be opened or punctured and a sample of liquid must be withdrawn. This renders the bottle useless for later measurements, greatly reducing the ability to see the bottle's differences in performance over time.

Accordingly, a need in the art exists for a method of determining carbonation loss in PET (polyethylene teraphtalate) or other forms of carbonated beverage bottles which is non-destructive, accurate, and facilitates an accurate prediction of shelf-life of the beverage bottle.

SUMMARY OF THE INVENTION

Accordingly it is a primary object of the present invention to provide a nondestructive method for testing carbonation loss in beverage bottles, such as PET or other plastic bottles, which is efficient and accurate.

It is another object of the present invention to provide a method for testing carbonation loss in beverage bottles which accounts for all mechanisms of loss: absorption, permeation, headspace growth and closure loss.

It is another object of the present invention to provide a method for predicting shelf-life of PET beverage bottles using IR spectroscopy wherein optimum wavelengths of infrared radiation are measured which provides useful and detectable carbonation concentration data over a wide range of pressures of $CO_2$ gas within the bottles.

It is still another object of the present invention to provide a method for measuring $CO_2$ gas concentration in beverage bottles using IR spectroscopy wherein the path length of the infrared test beam transmitted through the bottle is maintained substantially constant not withstanding a tendency for headspace growth within the beverage bottle.

The objects of the present invention are fulfilled by providing a method for measuring the concentration of $CO_2$ gas in a sealed container comprising the steps of: transmitting a beam of infrared radiation through the container and $CO_2$ gas therein; and selectively detecting the intensity of the infrared radiation transmitted therethrough in the range of wave numbers from about 4922 to about 5034 to thereby determine the concentration of $CO_2$ gas in the container.

In one embodiment the $CO_2$ gas being monitored is the $CO_2$ gas contained in the headspace above the carbonated liquid in the bottle. In another embodiment the test bottle is filled with compressed $CO_2$ gas. In this embodiment wherein the bottles are filled with compressed carbon dioxide gas, the need to shake the bottle to equilibrium is eliminated and the concentration of $CO_2$ gas is independent of temperature at the time of measurement.

In the method wherein the $CO_2$ gas measured is in the headspace of the bottle, the sidewall portions of the bottle surrounding the headspace are constrained at the time of measurement in order to maintain the shape and dimensions thereof substantially constant. This provides a constant path length for the transmitted beam of infrared radiation if it passes through these sidewall portions which are dimensionally stable. Without constraining the sidewall portions the shape of the sidewalls (the bottle diameter) will change, and thus the path length of the transmitted infrared beam will change adversely affecting the accuracy of the test results.

When the $CO_2$ being monitored is in the headspace of the beverage bottle, it is necessary to control, or account for, the temperature of the bottle in order to obtain accurate test results.

The measurement of carbonation in the headspace of a bottle via infrared absorption employs quantitative techniques using an infrared spectrophotometer, coupled with techniques developed according to the present invention in order to control, minimize, and compensate for numerous variables. These critical variables include temperature changes, ovality of the bottle, drift and instrument sensitivity, and headspace growth.

The foundation of the technique rests upon taking measurements at the proper wavelengths within the infrared spectrum. The present invention includes the discovery that the optimum wavenumbers of 4992 the peak height, and 5034 and 4922 for the base line are optimum wavelengths of infrared radiation which yield accurate and effective results in accordance with the method of the present invention with path lengths of 10–100 mm and concentrations of 10–100 PSI. This choice of wavelengths also allows the examination of carbonation in glass as well as PET and other plastic containers, whereas traditional mid-infrared techniques could not analyze this peak for a glass container. Measurements at other wavelengths are not successful because of too much or too little absorption of carbon dioxide, absorption by the bottle sidewall or the effects of water vapor. For example, it was attempted to test for carbonation loss in beverage bottles using the strongest absorption band for $CO_2$ gas at 4.3 microns. However, a problem was encountered at this wavelength because the infrared light was completely absorbed at relatively low concentration such as 10 PSI. Also, the small changes in concentration of $CO_2$ gas near 50 PSI could not be observed.

Beer's law provides the formula for converting absorption by $CO_2$ gas of infrared radiation into concentration of the $CO_2$ gas in the bottle or headspace. The variable in Beer's law which must be controlled to obtain accurate results includes the path length of the absorbed IR beam. If the shoulder area of bottle surrounding the headspace is out of round, or if the headspace creeps due to internal pressure over time, the corresponding increases in path length must be accounted for. In a preferred embodiment of the present invention, a fixture or clamp is utilized to hold the bottle sidewalls surrounding the headspace against at least two points of contact which maintain dimensional stability of the bottle sidewalls. The points of contact are at a fixed distance, and the beam of infrared radiation crosses immediately below these two points. Consequently, the path length is held substantially constant. In another approach changes in the outer diameter of the sidewalls of the bottle adjacent the headspace could be directly measured with a laser beam, and the dimensions detected could be utilized to compensate for changes in path length. However, it is preferable to utilize the fixture or clamp of the present invention to maintain a substantially constant path length of the IR beam through the bottle sidewalls surrounding the headspace at the time of measurement.

More specifically, Beer's law provides the following linear equation for infrared absorbtion:

$$A(v)=a(v)bc$$

Although $a(v)$ the absorbtivity, is a frequency-dependent molecular property, this is held constant according to the method of the present invention by taking measurements at the same selected peak absorbing frequency, namely, 2 microns or wavenumber 4992. The value b is the path length through the headspace of the bottle and c is the concentration of $CO_2$. The frequency is selected so that only $CO_2$ is measured. The partial pressure of air is ignored because it will not absorb at the same frequencies.

This simple equation of Beer's law provides several alternatives for interpreting the data. If the end result is to determine the percent loss over a time interval, no calibration is required to determine the constant $a(v)$, the absorbtivity. If the infrared beam passes through the bottle at points of negligible growth and headspace diameter, b, the path length, can be held constant as well. In this instance each absorption measurement will be directly related to concentration and a 1% decrease in absorption will signal a 1% loss of $CO_2$. Alternatively, if headspace diameter growth is significant, b can be accurately measured with existing equivalents such as a laser beam and concentration can subsequently be calculated.

In the embodiment of the present invention where the concentration of $CO_2$ gas in the head space of a container partially filled with carbonated beverage is being monitored, temperature greatly affects the results because the solubility of $CO_2$ is sensitive to temperature according to Henry's law. Also headspace concentration will vary with storage temperature over a period of weeks since the rate of transmission is a function of temperature. According to the present invention, temperature is controlled by storing the bottles in a temperature controlled environment. Before testing packages filled with the beverage, the bottles are submerged in a water bath in order to ensure uniform temperature for all bottles. During testing the temperature is monitored via the infrared heat it emits.

In order to compensate for instrument drift a glass calibration bottle may be used. The bottle is filled at atmospheric pressure with carbon dioxide and is sealed with a plastic closure. The concentration inside the glass bottle is virtually constant over a period of weeks, and the carbon dioxide peak is routinely monitored to obtain a reference signal related to background factors. To account for short term drift due to atmospheric carbon dioxide or temperature of the infrared spectrometer, background measurements may be taken before each measurement and subtracted from the test signals in order to remove background influences.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The objects of the present invention and the attendant advantages thereof will become more readily apparent by reference to the drawings wherein like reference numerals refer to like parts and wherein:

FIG. 5 is a flow chart of the method of the first embodiment of the present invention for measuring carbonation loss in a beverage bottle as illustrated in FIG. 1 wherein the $CO_2$ gas measured is in the headspace of the bottle above a carbonated liquid therein.

DESCRIPTION OF PREFERRED EMBODIMENTS

Figure 1:
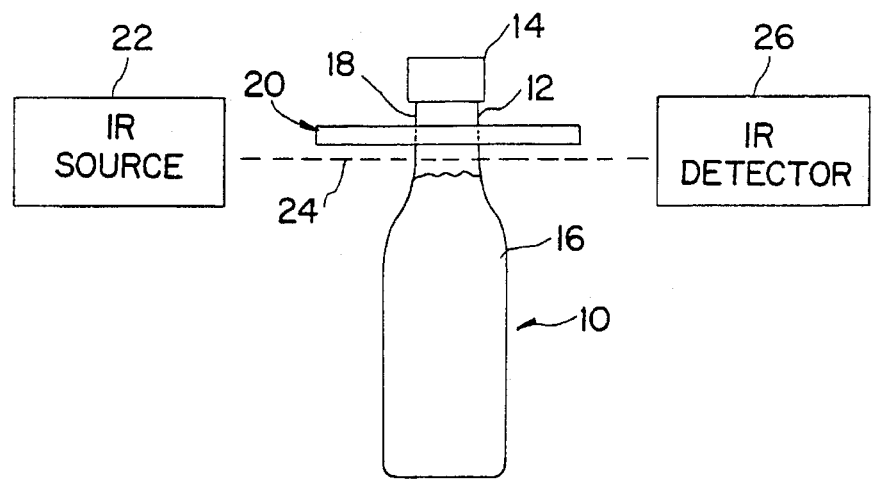
FIG. 1 is a diagrammatic illustration of a beverage bottle and infrared spectrophotometer for measuring the concentration of $CO_2$ gas in the headspace thereof in accordance with the present invention.
Figure 2:
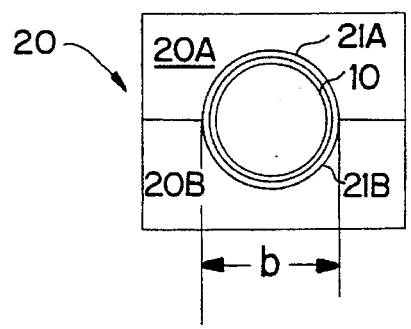
FIG. 2 is a top plan view of a portion of FIG. 1 illustrating how a fixture according to the present invention is utilized to clamp and constrain the sidewalls of the beverage bottle surrounding the head space to maintain the same dimensionally stable.

Referring to FIGS. 1 and 2 there is illustrated a beverage bottle 10 having a neck 12, a cap 14 and a carbonated liquid beverage 16 therein. A headspace 18 is formed above the liquid 16 and contains inter alia $CO_2$ gas in concentrations related to the carbonation level of the liquid 16. A source of infrared radiation 22 emits a test beam 24, which is transmitted through the sidewalls of the bottle and the headspace 18 to an infrared detector 26. A fixture or clamp 20 is provided to surround and constrain the sidewalls of the bottle in the headspace region 18 in order to maintain the diameter and shape of the sidewalls surrounding the headspace substantially constant. It is a discovery of the present invention that this is desirable in order to maintain a substantially constant path length b for the infrared test beam 24 passing through the sidewalls of the bottle and the headspace. As described hereinbefore, the provision of a constant path length is important in order to provide accurate results according to the formula provided by Beer's law.

Referring to FIG. 2, the fixture or clamp 20 may comprise a simple pair of movable plates 20A, 20B having semicircular cut-outs 21A, 21B, respectively. As illustrated in FIG. 2, such a simple clamping arrangement will support the sidewalls of the bottle being tested to maintain them substantially constant during measurements, in spite of changes in pressure of the gas in the headspace, which could result in dimensional instability of the sidewalls of plastic bottles, such as those of PET.

The infrared test beam 24 is aligned to pass as closely as possible beneath the fixture or clamp 20 in order to assure a constant path length.

Figure 3:
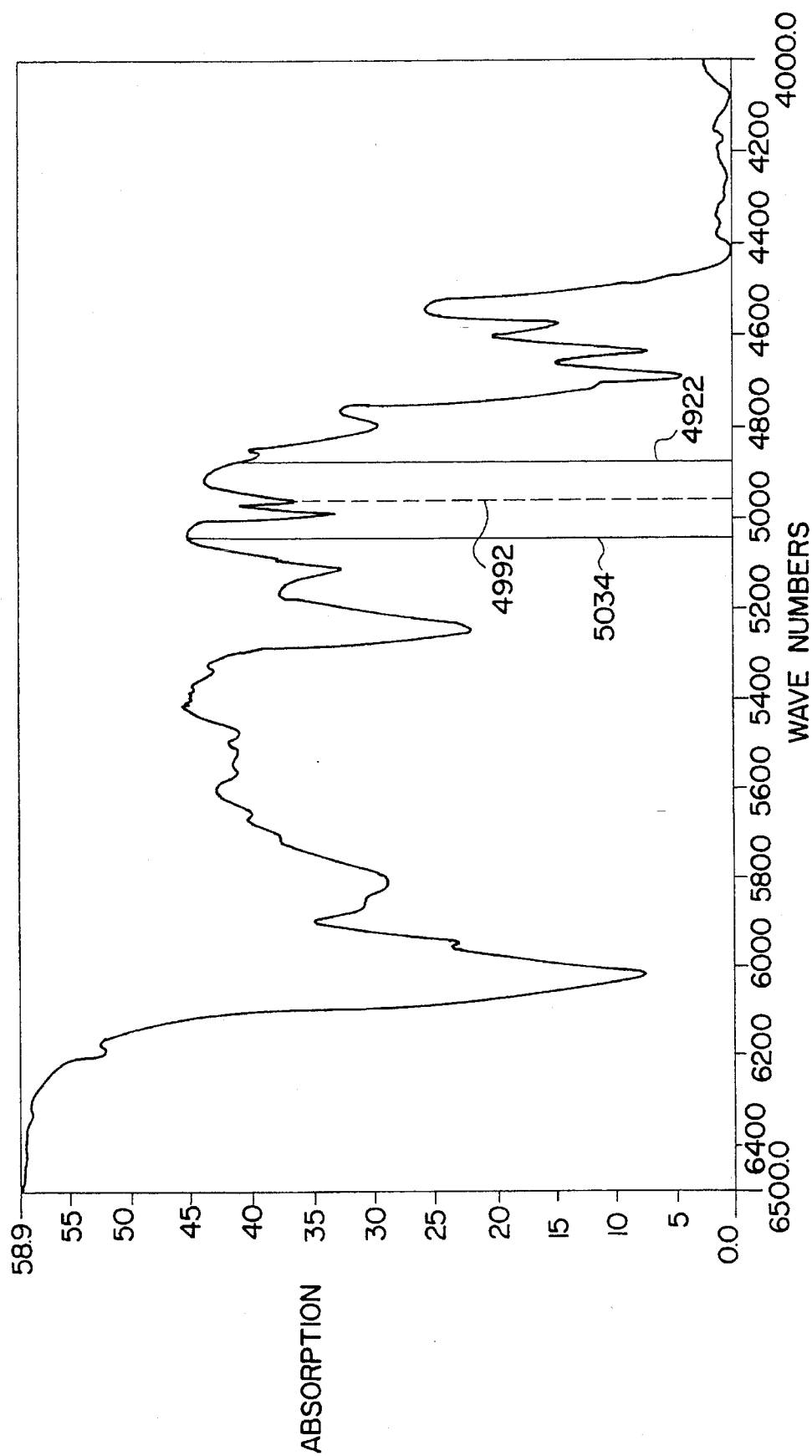
FIG. 3 is a graph showing absorption of infrared radiation versus wavenumbers and the optimum frequency range of measurement of infrared radiation between wavenumbers 4922 to 5034 in accordance with the present invention.

FIG. 3 illustrates the absorption values of infrared radiation passing through $CO_2$ gas over a wide range of wavenumbers. It is a discovery of the present invention that the optimum peak for infrared absorption measurement in accordance with the present invention is at a wavenumber of about 4992 and the optimum baseline numbers are at wavenumbers of 4922 and 5034. It has been found that these are the optimum wavelengths at which absorption by $CO_2$ gas should be measured to obtain accurate results over wide ranges of concentration of $CO_2$ gas, such as from about 10 PSI to about 100 PSI, and path lengths of 40–100 mm.

In accordance with the second embodiment of the present invention, the concentration of $CO_2$ gas in a container filled only with pressurized $CO_2$ gas is measured in order to predict carbonation loss for shelf-life of beverage bottles. This method has the advantage over bottles partially filled with carbonated liquid in that there is no need to shake the bottle to equilibrium and the concentration of $CO_2$ gas measured is independent of temperature at the time of measurement. Therefore, this is a much simpler test to implement.

Figure 6:
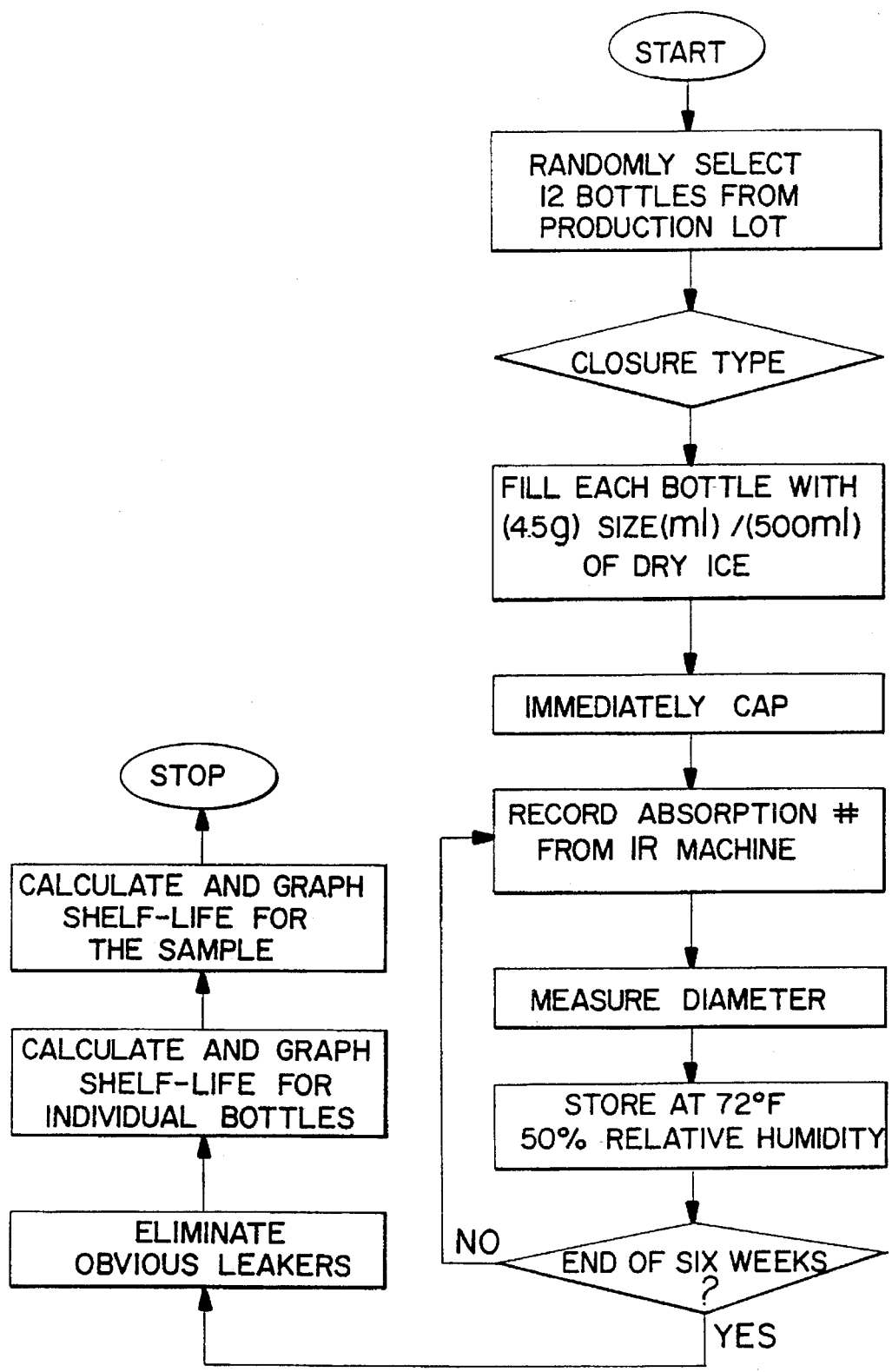
FIG. 6 is a flow chart of a method in accordance with a second embodiment of the present invention wherein the beverage bottle under test is filled only with compressed $CO_2$ gas.

A method for implementing this test procedure using compressed $CO_2$ gas is illustrated in the flow chart of FIG. 6. Initially, for example, twelve bottles (a "sample") are randomly selected from a production lot. A closure type of plastic, or aluminum is then selected. Each bottle is then filled with dry ice. For example, 4.5 grams of dry ice are provided for a 500 ml bottle. The bottle is then immediately capped, and the bottom is marked with an alignment mark so that it can be placed in the alignment mechanism of FIG. 4. The alignment mark on the bottom of the bottle is aligned with point C illustrated in FIG. 4, and the bottle is placed against walls A and B in the V-block 11. This alignment procedure is important to account for different dimensions of the bottle, e.g. the bottle may be slightly oval which would affect the path length of the infrared beam 24 if the bottle were not always aligned in the same position for each successive test.

Figure 4:
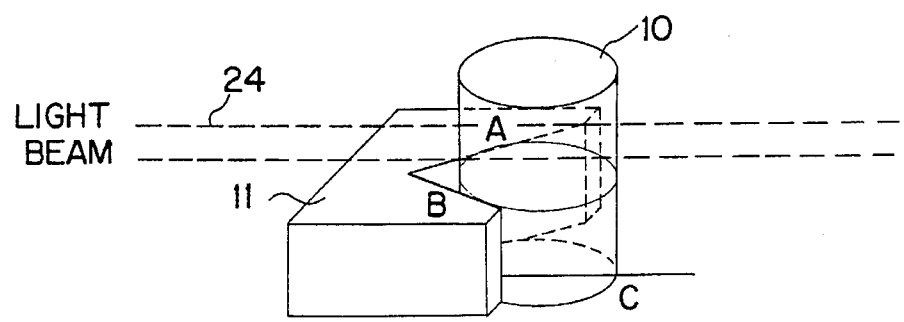
FIG. 4 is a diagrammatic view illustrating a second embodiment of the present invention in which only pressurized $CO_2$ gas is disposed in the beverage bottle under test and the bottle is disposed in an alignment fixture.

Once the bottle is aligned and inserted in the alignment device of FIG. 4, absorption values at the selected infrared wavelengths are recorded by the infrared spectrophotometer.

The diameter of the bottle at the point of measurement is also measured so that absorption can be calculated according to Beer's law. Bottles are then stored at 72° F., and 50% relative humidity for a period of six weeks and infrared absorption measurements are performed on the bottles three times a week. The bottles are then sorted to eliminate obvious leakers, and the remaining bottles have the shelf-life thereof predicted by calculating shelf-life according to the infrared absorption data collected. The shelf-life for individual bottles and the sample are then calculated and graphed and the procedure is complete.

The algorithms used to calculate shelf-life are quite simple. For an individual bottle, the percent loss in internal $CO_2$ is tracked over time. To obtain the shelf-life of sample size larger than a single bottle, the results for the individual bottles are averaged. For example, the shelf-life of a bottle with the following set of data can be calculated:

| Interval (days) | Absorption | DDiameter (mm) | Absorp./Diam. | % Loss |
|---|---|---|---|---|
| 0 | .334 | 60.0 | .00556 | 0 |
| 1 | .331 | 61.0 | .00542 | 2.5 |
| 10 | .325 | 61.5 | .00529 | 5.1 |
| 14 | .321 | 61.6 | .00521 | 6.4 |
| 18 | .318 | 61.6 | .00516 | 7.3 |
| 22 | .314 | 61.4 | .00511 | 8.1 |

The percent loss is simply the change in Absorption/Diameter after day 0. The linear regression from day 10 through the end of the test is calculated. The regression equations are straightforward. Any spreadsheet or statistical software will also calculate a linear regression.

The regression analysis on the summarized data presented above generates a constant of 2.93, X-coefficient of 0.234, and an $R^2$ of 0.976. If $R^2$ for the regression data is below 0.90, the data should be carefully evaluated for errors. If $R^2$ is below 0.87, the test should be considered invalid and run again.

To calculate the shelf life:

SL=shelf-life in days

M=X-coefficient or slope from regression analysis

C=constant from regression $$SL=\{17.5-C\}\div M$$

$$SL=\{17.5-2.93\}\div 0.2324=62.7$$

For this example, the shelf life is 62.7 days. The shelf-life corresponds to the drop in carbonation from 4.0 to 3.3 volumes, which is a 17.5 percent loss.

The method according to the first embodiment of the present invention illustrated in FIGS. 1 and 2 wherein the $CO_2$ concentration in the headspace in the bottle 10 is periodically measured in order to predict shelf-life is illustrated in the flow chart of FIG. 5. The process begins with the random selection of 12 bottles (a "sample") from a production lot. Again, the closure type is selected, such as plastic or aluminum. Each bottle is then filled to about 4.0 volumes with carbonated water and a headspace forms above the water in that portion of the bottle. The four bottles selected are then placed in a temperature controlled environment such as a water bath and stored for 24 hours. The bottles are then agitated or shaken in a vibration table for about 30 minutes in order to bring the distribution of $CO_2$ gas therein to equilibrium. Then a row of bottles is randomly selected, and a bottle from that row is randomly selected. That bottle becomes the test bottle, and it is agitated or shaken for approximately five seconds in order to bring the $CO_2$ gas and solution to equilibrium. An infrared test beam 24 is then passed through the headspace of the bottle while clamping the bottle with fixture 20 as illustrated in FIG. 1, and appropriate infrared absorption measurements are made at the peak wavelength illustrated in FIG. 3. This is repeated until the last bottle in a row has been tested. The temperature at which the bottles were tested is then recorded and the process proceeds with the testing of other rows of bottles and all bottles in that row in a similar fashion until absorption values for all of the bottles have been recorded. At the end of six weeks after each bottle has been tested, shelf life for each bottle and the sample are calculated using an appropriate algorithm as described above in connection with FIG. 6.

The methods of the present invention have been described herein using a PET bottle as the test bottle since this is the most commonly used plastic bottle in the beverage industry. However, other types of plastic bottles can be tested for shelf-life with the methods of the present invention. Other types of plastic bottles may include bottles made from polyethylene napthalate (PEN), COPET, polyvinyl chloride, or acrylonitrile. COPET is simply PET copolymer made with a mixture of isopthalic acid and terapthalic acid.

PET bottles with barrier coatings such as Seran, epoxy, or polyurethane, EVOH, or silicon dioxide can also be measured. All of these barrier films are thin enough to allow much more than 20 percent transmission from 4922 to 5034 wavenumbers.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for measuring the concentration of $CO_2$ gas in a sealed container comprising the steps of:

transmitting a beam of infrared radiation through the container and $CO_2$ gas therein; and selectively detecting the intensity of the infrared radiation transmitted therethrough in the range of wavenumbers from about 4922 to about 5034 to thereby determine the concentration of $CO_2$ gas in the container.

2. The method of claim 1 wherein the intensity of infrared radiation transmitted at a wavenumber of about 4992 is selectively detected to determine the concentration of $CO_2$ gas.

3. The method of claim 1 wherein the intensity of infrared radiation transmitted at a wavenumber of about 4991 is selectively detected to determine the concentration of $CO_2$ gas.

4. A method of non-destructively measuring carbonation of a liquid in a sealed container, the container containing the liquid up to a certain level and a headspace thereabove with $CO_2$ gas therein; comprising the steps of:

transmitting a beam of infrared radiation through the headspace and the $CO_2$ gas therein; and selectively detecting the intensity of the infrared radiation transmitted therethrough in the range of wavenumbers from about 4922 to about 5034 to thereby determine the concentration of $CO_2$ gas in the headspace and the carbonation of the liquid.

5. A method of predicting shelf-life of carbonated liquids in bottles by periodically measuring the concentration of $CO_2$ gas in the headspace of the bottle, comprising the steps of:

a) constraining sidewall portions surrounding the headspace at the time of measurement in order to maintain the shape and dimensions thereof substantially constant;

b) transmitting a beam of infrared radiation through said sidewall portions surrounding the headspace and the $CO_2$ gas therein;

c) selectively detecting the intensity of the infrared radiation transmitted therethrough to thereby determine the concentration of $CO_2$ gas in the headspace and the carbonation of the liquid; and d) periodically repeating steps a) to c) over a predetermined period of time and collecting data relating to the carbonation of the liquid; and e) calculating a predicted shelf-life from that data.

6. The method of claim 5 comprising the further steps of:

controlling the temperature of the bottle; and periodically repeating said steps a) to c) with the bottle at substantially the same temperature.

7. The method of claim 6 comprising the further step of agitating the bottle for a predetermined period of time prior to periodically performing said steps a) to c).

8. The method of claim 7 wherein said predetermined period of time is about 5 seconds.

9. The method of claim 5 comprising the further step of agitating the bottle for a predetermined period of time prior to periodically performing said steps a) to c).

10. The method of claim 9 wherein said predetermined period of time is about 5 seconds.

11. The method of any one of claims 5 to 10 wherein the infrared radiation is selectively detected in the range of wavenumbers from about 4922 to about 5034.

12. The method of claim 11 wherein the infrared radiation selectively detected is about 4992.

13. A method of predicting shelf-life of carbonated liquids in bottles by periodically measuring the concentration of $CO_2$ gas in the bottle, comprising the steps of:

a) filling the bottle with a predetermined quantity of dry ice;

b) applying a cap to the bottle to hermetically seal the dry ice therein;

c) transmitting a beam of infrared radiation through selected sidewall portions of the bottle and the $CO_2$ gas therein;

d) selectively detecting the intensity of the infrared radiation transmitted therethrough to thereby determine the concentration of $CO_2$ gas in the bottle;

e) periodically repeating steps c) and d) over a predetermined period of time and collecting data relating to the concentration of $CO_2$ gas in the bottle; and f) calculating a predicted shelf-life of carbonated liquids from that data.

14. The method of claim 13 wherein the infrared radiation is selectively detected in the range of wavenumbers from about 4922 to about 5034.

15. The method of claim 14 wherein the infrared radiation selectively detected is about 4992.

16. A method of predicting shelf-life of carbonated liquids in bottles by periodically measuring the concentration of $CO_2$ gas in the bottle, comprising the steps of:

a) filling the bottle with $CO_2$ gas;

b) transmitting a beam of infrared radiation through selected sidewall portions of the bottle and the $CO_2$ gas therein;

c) selectively detecting the intensity of the infrared radiation transmitted therethrough to thereby determine the concentration of $CO_2$ gas in the bottle;

d) periodically repeating steps b) and c) over a predetermined period of time and collecting data relating to the concentration of $CO_2$ gas in the bottle; and e) calculating a predicted shelf-life of carbonated liquids from that data.

17. The method of claim 16 wherein the infrared radiation is selectively detected in the range of wavenumbers from about 4922 to about 5034.

18. The method of claim 17 wherein the infrared radiation selectively detected is about 4992.

* * * * *